United States Patent [19]

Rosenberg et al.

[11] Patent Number: 5,741,519

[45] Date of Patent: Apr. 21, 1998

[54] THE PRODUCTION OF ACTIVE SUBSTANCE COMPOSITIONS IN THE FORM OF A SOLID SOLUTION OF THE ACTIVE SUBSTANCE IN A POLYMER MATRIX, AND ACTIVE SUBSTANCE COMPOSITIONS PRODUCED BY THIS PROCESS

[75] Inventors: Joerg Rosenberg, Ellerstadt; Jörg Breitenbach, Mannheim, both of Germany

[73] Assignee: BASF Aktiengesellschaft, Ludwigshafen, Germany

[21] Appl. No.: 737,745

[22] PCT Filed: Mar. 12, 1996

[86] PCT No.: PCT/EP96/01047

§ 371 Date: Nov. 21, 1996

§ 102(e) Date: Nov. 21, 1996

[87] PCT Pub. No.: WO96/29061

PCT Pub. Date: Sep. 26, 1996

[30] Foreign Application Priority Data

Mar. 21, 1995 [DE] Germany .................. 195 09 807.2

[51] Int. Cl.$^6$ .................. A61K 9/20; A61K 9/14
[52] U.S. Cl. .................. 424/464; 424/465; 424/468; 424/469; 424/486; 424/487; 424/488; 424/484; 424/489; 424/499; 424/500; 264/6; 264/141; 264/176.1; 264/211.21; 264/211

[58] Field of Search .................. 424/464, 465, 424/468, 469, 486, 487, 488, 484, 489, 499, 500; 264/6, 141, 176.1, 211.21, 211

[56] References Cited

U.S. PATENT DOCUMENTS

| 4,880,585 | 11/1989 | Klimesch et al. ............ 264/141 |
| 5,073,379 | 12/1991 | Klimesch et al. ............ 424/467 |
| 5,456,923 | 10/1995 | Nakamichi et al. ............ 424/489 |

FOREIGN PATENT DOCUMENTS

| 580 860 | 2/1994 | European Pat. Off. |
| 661 045 | 7/1995 | European Pat. Off. |
| 1 766 546 | 6/1968 | Germany. |
| WO 94/06414 | 3/1994 | WIPO. |

OTHER PUBLICATIONS

Kearney et al., Int. Journal of Pharm., 104, 169–174 (1994).
Kondo et al., Journal of Pharm. Sciences, 83, 566–570 (1994).

*Primary Examiner*—Frederick Krass
*Attorney, Agent, or Firm*—Keil & Weinkauf

[57] ABSTRACT

A process for producing active substance compositions in the form of a solid solution of the active substance in a polymer matrix, which comprises melt extrusion of the active substance in nonionic form together with a polymer and a salt.

6 Claims, No Drawings

THE PRODUCTION OF ACTIVE SUBSTANCE COMPOSITIONS IN THE FORM OF A SOLID SOLUTION OF THE ACTIVE SUBSTANCE IN A POLYMER MATRIX, AND ACTIVE SUBSTANCE COMPOSITIONS PRODUCED BY THIS PROCESS

The present invention describes a process for producing active substance compositions in which the active substance is present in a molecular dispersion in a polymer matrix, and active substance compositions produced thereby.

Melt extrusion processes for producing drug forms (tablets, pellets, granules) are described in the literature. The combination of an extrusion step with a subsequent shaping step, in particular, makes this process a very straightforward, because single-stage (and thus cost-saving), method for producing drug forms such as tablets (DE-A-1 766 546 and U.S. Pat. No. 4,880,585). These and other references (EP-A-580 860) mention that the thermal processing during the extrusion cause the active substance, owing to the melting, to be incorporated in the form of a molecular dispersion into the likewise molten polymer melt. This is manifested by the fact that clear transparent melts containing active substances are formed, and these usually do not recrystallize after these compositions have been cooled to room temperature, but on the contrary maintain their molecular dispersion.

These formulations are generally referred to as solid solutions and have been described many times per se in the literature (eg. A. S. Kearny et al.; Int. J. Pharm. 104 (1994), 169–174). However, they have to date been produced by melt extrusion processes in only a few cases. Solid solutions are also often produced by a process in which the components are dissolved in an organic solvent, and the solvent is then stripped off again. This has the disadvantage that organic solvents inevitably have to be employed. In addition, these (multistage) processes cannot be carried out continuously, and the homogeneity achieved is unsatisfactory.

Molecular dispersion of an active substance in a water-soluble polymer is a method which has been described many times for increasing the rate of dissolution of a (sparingly soluble) active substance in aqueous media. It has in many cases emerged, especially with sparingly soluble active substances, that absorption of the latter from the gastrointestinal tract after oral administration was impossible or possible to only a very small extent because the rate of dissolution of the active substance was too slow. However, only an active substance which is dissolved (in the aqueous medium) can be absorbed. It is possible, however, with the aid of a molecular dispersion of the active substance in a water-soluble polymer considerably to speed up this process because individual molecules of active substance are released from these formulations directly in the dissolving process of the (water-soluble) formulation, in contrast to previous preparations which contain crystals of active substance whose kinetics of dissolution are considerably slower. Such solid solutions therefore in many cases lead to a distinct increase in the proportion of active substance which can be absorbed, which in many cases leads to improvements in the bioavailability of a (sparingly soluble) active substance (N. Kondo et al., J. Pharm. Sci. 83 (1994), 566–570).

However, it is not possible to prepare solid solutions of all active substances.

The formation of solid solutions by thermal processes such as extrusion (in contrast to the normally employed processes via organic solvents) is subject to various preconditions which must be met at least in part:

a) the melting point of the active substance must be so low that at the temperatures generally prevailing during the extrusion intensive mixing of the two substances in the melt (active substance and polymer) is possible, and/or b) the rate of dissolution of a (high-melting) active substance in the polymer melt is so high that it is possible for solid solutions to form despite the relatively short residence time in the extruder.

The latter point in particular is not complied with in most cases of high-melting active substances because the residence time of the composition in the extruder is too short (generally below one minute). An increase in this residence time leads to (thermal) damage to the active substance and/or polymer and is therefore not practicable.

However, a considerable proportion of known active substances comprises ionic active substances which are employed in the form of their salts. In virtually all these cases, the salt formation results in a distinct increase in the melting point, and this was always desirable for the processibility of the substances by conventional techniques. Starting from the active substance in nononic form it is possible to convert it into the form of a molecular dispersion because the low melting point of the latter means that, in contrast to the salt form, it can be melted on extrusion and can then easily be mixed intensively with the likewise molten polymer to give the molecular dispersion.

Formulations which contain the active substance in nonionic form are, however, disadvantageous in many cases, because it is often only the corresponding salts of the active substance which have sufficient solubility in the aqueous medium. This means that although there is rapid release of the (molecular) active substance from the solid solutions in the drug form (eg. tablets), there is in this case no release of a salt which is readily soluble in water, so that recrystallization may rapidly occur. However, sufficient solubility in water is indispensable inter alia to make satisfactory absorption possible.

It is an object of the present invention to provide a single stage process which can be operated continuously to produce active substance compositions with an active substance which is very well absorbed, where the active substance is, on the one hand, in salt form and, on the other hand, in a molecular dispersion, without the need to employ solvents in the production.

We have found that this object is achieved by a process for producing active substance compositions in the form of a solid solution of the active substance in a polymer matrix, which comprises melt extrusion of the active substance in nonionic form together with the polymer and a salt.

The invention likewise relates to the active substance compositions produced by the process according to the invention, which are distinguished by particularly good homogeneity of the ingredients.

Water-soluble polymers are preferably employed in the process according to the invention.

It is possible very simply with the process according to the invention to add the counterion corresponding to the active substance in the form of a suitable (generally inorganic) salt likewise to the (powder) mixture to be extruded. This makes it possible for the first time, starting from the nonionic active substance (eg. deprotonated amine or protonated carboxylic acid), to achieve, owing to the thermal processing (extrusion), an intensive mixing of the two melts (active substance and polymer), and to produce, at the same time or subsequent thereto, by adding an additional, acidic or alkaline salt, the required ionic active substance component even during the extrusion process, quasi in situ.

This novel process principle makes it possible for the first time to produce molecular dispersions of active substance salts in water-soluble polymers via the nonionic, low-melting form and to obtain very homogeneous dispersions. Hitherto these preparations could not be produced in this form by the purely thermal process of extrusion, as a consequence of their melting point being too high, so that it was necessary to have recourse to the conventional solvent process.

Examples of active substances which can be employed are:

acetylcysteine, acetylsalicylic acid, ambroxol, atenolol, biperiden, clavulanic acid, cromoglicic acid, diltiazem, dopamine, ephedrine, flurbiprofen, ibuprofen, lidocaine, metoprolol, methylephedrine, naftidrofuryl, nicotinic acid, pantothenic acid, propafenone, propranolol, pseudoephedrine, salicylic acid, sotalol, valproic acid and verapamil.

In a few cases it is also possible for the novel process to be used to make active substances which have hitherto been administered predominantly in their nonionic form more bioavailable by specific salt formation. One example of this is the active substance ibuprofen, which carries a (protonated) carboxyl group. Ibruprofen is employed for the therapy of pain, which generally requires a rapid onset of action (eg. headache tablet). However, the precondition for rapid display of the action is that the active substance rapidly dissolves after oral administration (eg. after taking a tablet) so that the following absorption can take place rapidly. Thus, preparations with a high rate of dissolution of the active substance are advantageous in this case. Solid solutions based on the nonionic active substance, which even on their own contribute to rapid solubilization, are described in the literature (EP-A-580 860). However, these preparations have disadvantages because the active substance is present in the nonionic form which has low solubility in water, which in fact makes it possible to prepare the solid solutions. On the other hand, the salts with better solubility in water are required for rapid therapy.

These previously disclosed formulations based on solid solutions can be improved by using the process according to the invention via specific salt formation because ibuprofen salts have better solubility in water than the nonionic active substance. This increases the rate of release of active substance from the drug form (eg. tablet), as can easily be shown by the in vitro release method conventional for this purpose.

Ibuprofen preparations which contain the active substance as salt are described in the literature (eg. lysinate or sodium salts), and the faster onset of action of these preparations compared with formulations which contain the nonionic active substance has been clinically proven in the particular case of the lysinate salt (G. Geisslinger et al., Drug Investigation 5 (1993), 239 ff). The novel process according to the invention now makes it possible to make such formulations (eg. lysinate) directly from the nonionic active substance in the production of the drug without the need first to synthesize the particular active substance salt in a separate step. In the case of ibuprofen, for example, it has emerged that addition of, for example, sodium acetate made it possible to solubilize ibuprofen as solid solution in a polymer matrix composed of vinylpyrrolidone/vinyl acetate copolymer in the form of a clear melt.

The producibility of formulations by the process according to the invention depends crucially on the solubility of the active substance in the water-soluble polymer. Water-soluble polymers which are particularly preferred are thus naturally those which are known as solvents for a large number of active substances. These include, particularly preferably, the polyvinylpyrrolidones (homo- and copolymers) mentioned in DE 1 766 546 and U.S. Pat. No. 4,880,585. Also preferred are polyethylene glycols and polyethylene oxides, and hydroxyalkylcelluloses such as hydroxypropylcelluloses. Also preferred are cellulose derivatives which carry carboxyl substituents, such as cellulose acetate phthalate (CAP), which are insoluble in acidic medium (gastric fluid pH 1) and dissolve only at the higher pH values (pH 6–7) in the small intestine. The use of these polymers makes such preparations resistant to gastric fluid owing to the absence of release of active substance in the stomach, which makes it possible for acid-labile active substances, for example, to reach the small intestine intact, where they can be absorbed unchanged (cf. R. Voigt; Lehrbuch der pharmazeutischen Technologie; Verlag Chemie 1984, page 209 ff). Also preferred are methacrylic acid polymers, especially copolymers of methyl methacrylate and ethyl acrylate which additionally contain up to about 15% of trimethylammoniomethyl acrylate chloride. All these polymers can be present alone or in mixtures, which allows the properties of the formulations made in this way to be influenced in a specific manner. It is crucial for utilizability that the chosen active substance is sufficiently soluble in the polymer matrix. In general, this can be assessed purely visually by the appearance of the melt containing the active substance and leaving the extruder. Solid solutions are evident from clear, absolutely transparent melts which retain their optical transparency even after cooling to room temperature. The absence of crystalline residues of active substance can then be confirmed by physical methods such as differential thermal analysis.

The process according to the invention can preferably be employed for those active substances capable of salt formation but having such high melting points in the form of their salts which are preferably employed that it was not possible with the extrusion processes disclosed to date to produce formulations with molecular dispersions of the active substance. Conventional extrusion temperatures are in the range from 60° to 160° C., preferably from 80° to 140° C. The active substance ought therefore to have in the nonionic form a melting point which preferably does not exceed 140° C. Markedly lower melting points are possible; even active substances which are liquid or oily at room temperature can be used. In these cases, either there can be previous adsorption on solid carriers (eg. lactose, silica gels or the like), or else the active substance is metered as liquid through pumps directly into the extruder by processes known in plastics technology, eg. through high pressure pumps (lateral feeding).

Suitable as salt component are a wide variety of organic and inorganic salts. Those preferred for anionic active substances (eg. active substances carrying carboxyl groups) are sodium salts of carboxylic acids such as sodium acetate, succinate, aspartate, maleate, glycinate, lysinate, citrate, lactate, gluconate and tartrate, and sodium salts of inorganic compounds such as disodium hydrogen phosphate, sodium dihydrogen phosphate and trisodium phosphate. Acidic salts are preferred for cationic active substances (eg. active substances carrying amino groups), such as hydrochlorides of amino acids, but also carboxylic acids such as acetic acid, succinic acid, aspartic acid, malic acid, glycine, lysine, citric acid, lactic acid, gluconic acid and tartaric acid.

The amount of the salt component is essentially determined by the amount of nonionic active substance.

It is possible to add to the formulations according to the invention various other pharmaceutically conventional ancillary substances in order, for example, to influence the processability or other properties in a specific manner. These ancillary substances include, for example, fillers (eg. lactose, mannitol), lubricants (eg. mono-, di- and triglycerides, and salts of fatty acids), mold release agents (eg. lecithin), plasticizers (eg. fatty acids, fatty alcohols or triethyl citrate), stabilizers (eg. antioxidants such as ascorbic acid or butylated hydroxytoluene), dyes or pigments (eg. iron oxide pigments), disintegrants (eg. crosslinked polyvinylpyrrolidone, microcrystalline cellulose), preservatives (eg. sorbic acid), or flavorings (eg. flavors, sweeteners). An important precondition for the choice of these ancillary substances is adequate (thermal) stability in the chosen process (extrusion). It is furthermore necessary to ensure that the presence of other ancillary substances does not reduce the amount of polymer below the minimum necessary to solubilize the active substance, because there may otherwise be recrystallization of the active substance in the matrix, which becomes evident from cloudiness.

The preparations according to the invention are produced in conventional processes, preferably in single or twin screw extruders, with particular preference for corotating twin screw extruders because their mixing action is more intensive. Shaping of the melts containing active substance can take place in a variety of ways. Direct melt calendering, for example to tablets, is possible as described in EP-A 240 906. It is likewise possible to produce pellets by cutting thin extrudates with rotating knives as described in DE-A 38 30 355. Both processes have the advantage that they can be carried out continuously and directly after the extrusion step (quasi on-line). However, it is also possible to allow the extruded melts to cool and only then to carry out further steps for shaping, eg. milling to granules which can be used for instant drinks or which can be packed in hard gelatin capsules or compressed to tablets. The compositions according to the invention are generally employed as drugs. However, it is also possible to process active substances which are known, for example, for the treatment of plant diseases and for eradicating insects by the process according to the invention. Active substances for the purpose of the process according to the invention also include vitamins and minerals (eg. trace elements).

The following examples illustrate the invention.

EXAMPLE 1

(Comparative Example)

A powder mixture consisting of 20.0% by weight of ibuprofen (nonionic) and 80% by weight of vinylpyrrolidone/vinyl acetate copolymer (Kollidon VA-64 (BASF)) was extruded in a twin screw extruder (ZSK-30, Werner and Pfleiderer) to give a clear transparent melt. The melt was compressed immediately after leaving the extruder to oblong tablets weighing about 1000 mg with the aid of a molding calender by the process disclosed in U.S. Pat. No. 4,880,585. The extrusion conditions were set as follows:

| Temperature of section 1 | 50° C. |
|---|---|
| Temperature of section 2 | 85° C. |
| Temperature of section 3 | 125° C. |
| Temperature of section 4 | 100° C. |
| Temperature of section 5 | 100° C. |
| Temperature of head | 90° C. |
| Temperature of dies | 80° C. |

Release of active substance from these tablets was determined by the USP paddle method in 900 ml of phosphate buffer (pH 7.5) at 37° C. with a paddle speed of 100 rpm. The concentrations of active substance in the test solution were determined by UV spectroscopy.

The following releases of active substance were obtained:

after 10 minutes: 35.9% after 20 minutes: 65.7% after 30 minutes: 84.3% after 60 minutes: 100%

EXAMPLE 2

A powder mixture consisting of 20.0% by weight of ibuprofen (nonionic), 75.0% by weight of Kollidon VA-64 and 5.0% by weight of sodium acetate trihydrate was extruded under the following conditions in a twin screw extruder (ZSK-30, Werner and Pfleiderer) to give a clear transparent melt:

| Temperature of section 1 | 50° C. |
|---|---|
| Temperature of section 2 | 80° C. |
| Temperature of section 3 | 110° C. |
| Temperature of section 4 | 90° C. |
| Temperature of section 5 | 90° C. |
| Temperature of head | 80° C. |
| Temperature of dies | 80° C. |

The release of active substance from the oblong tablets weighing about 1000 mg obtained as in Example 1 was determined by the same method:

after 10 minutes: 48.1% after 20 minutes: 77.8% after 30 minutes: 95.2% after 60 minutes: 100%.

We claim:

1. A process for producing biologically active substance compositions in the form of a solid solution of the active substance in a polymer matrix, where the biologically active substance is in salt form, which comprises melt extrusion of the biologically active substance, which is capable of forming a salt, in nonionic form together with a polymer and an effective amount of a salt which provides the counterion forming the salt of the biologically active substance.

2. A process as claimed in claim 1, wherein a water-soluble polymer is employed.

3. A process as claimed in claim 2, wherein polyvinylpyrrolidone, a vinylpyrrolidone/vinyl acetate copolymer or hydroxyalkylcellulose is employed.

4. A biologically active substance composition comprising an active substance in the form of a solid solutiion of its salt in a polymer matrix, obtained by the process claimed in claim 1.

5. The process of claim 1 wherein the biologically active substance is a drug.

6. The composition of claim 4 wherein the biologically active substance is a drug.

* * * * *